US005463117A

United States Patent [19]
Stroppolo et al.

[11] Patent Number: 5,463,117
[45] Date of Patent: Oct. 31, 1995

[54] PROCESS FOR THE PREPARATION OF SALTS OF 2-(4-ISOBUTYLPHENYL)PROPIONIC ACID

[75] Inventors: Federico Stroppolo, Pregassona, Switzerland; Daniele Bonadeo, Varese; Annibale Gazzaniga, Rescaldina, both of Italy

[73] Assignee: Zambon Group S.p.A., Vicenza, Italy

[21] Appl. No.: 281,670

[22] Filed: Jul. 29, 1994

[30] Foreign Application Priority Data

Jul. 30, 1993 [IT] Italy ................................. MI93A1721

[51] Int. Cl.$^6$ ............................................. C07C 53/134
[52] U.S. Cl. ............................................................ 562/496
[58] Field of Search ............................................... 562/496

[56] References Cited

U.S. PATENT DOCUMENTS 4,279,926  7/1981  Bruzzese et al. .
4,689,218  8/1987  Gazzaniga et al. .
4,834,966  5/1989  Gazzaniga et al. .
5,200,558  4/1993  Kwan ..................................... 562/496
5,332,834  7/1994  Bhattacharga ......................... 562/496

FOREIGN PATENT DOCUMENTS 0643168   5/1992  Australia .
0424028A2 4/1991  European Pat. Off. .
1471910   4/1977  United Kingdom .
94/12451  6/1994  WIPO .

OTHER PUBLICATIONS

CA 84:5394 1975.
CA 106:78438 1986.
The Merick Index, Eleventh Edition, 1989, p. 776.

Primary Examiner—Paul J. Killos
Attorney, Agent, or Firm—Oblon, Spivak, McClelland, Maier & Neustadt

[57] ABSTRACT

A process for the preparation of salts of 2-(4-isobutylphenyl)propionic acid with basic aminoacids, in particular L-arginine and L-lysine, is described.

10 Claims, No Drawings

PROCESS FOR THE PREPARATION OF SALTS OF 2-(4-ISOBUTYLPHENYL)PROPIONIC ACID

The present invention relates to a process for the preparation of salts of 2-(4-isobutylphenyl)propionic acid and, more particularly, it relates to a process for the preparation of salts of 2-(4-isobutylphenyl)propionic acid with basic aminoacids.

2-(4-isobutylphenyl)propionic acid is a known nonsteroidal anti-inflammatory drug (Merck Index, XI ed., No. 4812, page 776) whose international nonproprietary name is Ibuprofen.

Ibuprofen is widely used in therapy for its analgesic, anti-inflammatory and antipyretic properties, in the racemic form that is in the form of S-Ibuprofen and R-Ibuprofen enantiomer mixture.

It is already known from many years that S-Ibuprofen is the pharmacologically active enantiomer of Ibuprofen.

From now on, if not otherwise specified, with the term Ibuprofen we will intend to refer both to the racemate (RS-Ibuprofen) and to the single enantiomers (S-Ibuprofen and R-Ibuprofen).

Ibuprofen is a molecule poorly soluble in water and that makes it not very suitable for some formulation and administration forms. Therefore, the salts of Ibuprofen which give improved solubility characteristics to the active principle and, in particular, the salts of Ibuprofen with basic aminoacids have been much studied.

British patent No. 1,471,910 (Neopharmed S.p.A.) describes the salts of RS-Ibuprofen with lysine.

U.S. Pat. No. 4,279,926 (SPA-Societ`a Prodotti Antibiotici S.p.A.) describes the salts of RS-Ibuprofen with basic aminoacids, in particular with lysine, arginine and ornithine.

European patent application No. 424,028 (Merck & Co. Inc.) describes the salts of S-Ibuprofen with basic aminoacids such as lysine, arginine and histidine.

In the cited patent documents the preparation and isolation of the salts of Ibuprofen with basic aminoacids is carried out by dissolution and precipitation from organic solvents (acetone and ethanol or mixtures thereof) or, preferably, from mixtures of water and alcohol (ethanol) or of water and acetone.

It is clear that the drawbacks showed by these methods for the preparation of the salts of Ibuprofen with basic aminoacids are numerous, mainly in their applicability on industrial scale.

First of all, the yields are not always high and the employed volumes are high so as to cause low productivity in the whole process. The use of organic solvents implies the need of further purifications to remove them or to maintain the traces of residual solvents in the finished product under the acceptable levels.

We have now found that the salts of Ibuprofen with basic aminoacids may be advantageously prepared by a simple and cheap method having industrial applicability, with practically quantitative yields and without using any organic solvent.

It is therefore the object of the present invention a process for the preparation of salts of Ibuprofen with basic aminoacids comprising the admixture of equimolar amounts of Ibuprofen and of a basic aminoacid in water and the isolation of the salt of Ibuprofen with the basic aminoacid by removal of the water from the mixture. Preferably the Ibuprofen of RS-Ibuprofen or S-Ibuprofen.

The basic aminoacid is selected among L-arginine, L-lysine, L-ornithine, L-histidine, D-arginine, D-lysine, D-ornithine, D-histidine, DL-arginine, DL-lysine, DL-ornithine and DL-histidine.

Preferably the basic aminoacid is selected between L-arginine and L-lysine.

The isolation of the salt of Ibuprofen with the basic aminoacid is carried out, preferably, by removing the water from the mixture by heating or under vacuum.

The amount of water to be used in the process object of the present invention is not a critical factor.

However it is important to underline that a small amount of water is sufficient.

Preferably the amount of water is comprised between 0.4 and 1.5 parts by weight with respect to the amount of Ibuprofen.

Still more preferably the amount of water is equal to about 0.5 parts by weight with respect to the amount of Ibuprofen.

A practical application of the process object of the present invention is the following.

Ibuprofen is put into a mixing-machine and heated up to melting. Boiling water is added under stirring and an equimolar amount of basic aminoacid is added too. The mixture is mixed up to obtain a homogenous mass and the water is evaporated.

The salt of Ibuprofen with basic aminoacid is obtained with quantitative yields and high purity (superior to 99.5%) and may be directly formulated into a suitable pharmaceutical composition without requiring any further purification.

The process object of the present invention involves a great number of advantages with respect to the processes described in literature. The use of the water as unique solvent avoids the problems bound to the use of organic solvents such as the possible presence of toxic residues into the finished product and the need to adopt particular arrangements during the work-up (for inflammability and toxicity). Moreover, in the process object of the present invention water is used in very small amount.

This feature, combined with the quantitative yield, gives to the process a high degree of productivity thus making it particularly advantageous from the economical point of view.

As already underlined, the salt of Ibuprofen with basic aminoacid is directly obtained with a high purity and therefore it does not require further purifications and it may be directly formulated into a suitable pharmaceutical composition.

Another important feature of the process object of the present invention is the extreme simplicity in its practical realization.

The whole process requires short times and may be carried out in a single vessel.

With the aim to better illustrate the present invention the following examples are now given.

EXAMPLE 1

Preparation of the salt of RS-Ibuprofen with L-arginine

RS-Ibuprofen (412.54 g) is put into a planetary mixing-machine and heated up to melting.

Boiling water (about 206 g) is added under stirring.

L-arginine (346.8 g) is then added always under stirring.

The mixture is mixed up to obtain a creamy and homogenous mass.

The mass is then dried in oven.

The salt of RS-Ibuprofen with L-arginine (quantitative yield) is obtained and the thermic and spectroscopic analysis show a purity higher than 99.5%.

EXAMPLE 2

Preparation of the salt of S-Ibuprofen with L-arginine

S-Ibuprofen (412.54 g) is put into a mixing-machine and heated up to melting.

Boiling water (about 206 g) is added under stirring.

L-arginine (346.8 g) is then added always under stirring.

The mixture is mixed up to obtain a creamy and homogenous mass.

Vacuum is applied inside the mixing-machine and the content is dried affording the salt of S-Ibuprofen with L-arginine (quantitative yield) showing a purity higher than 99.5% at the thermic and spectroscopic analysis.

EXAMPLE 3

Preparation of the salt of RS-Ibuprofen with L-lysine

RS-Ibuprofen (412.54 g) is put into a mixer-machine and heated up to melting.

Boiling water (about 206 g) is added under stirring.

L-lysine (292.68 g) is then added always under stirring.

The mixture is mixed up to obtain a creamy and homogenous mass.

Vacuum is applied inside the mixing-machine and the content is dried affording the salt of RS-Ibuprofen with L-lysine (quantitative yield) showing a purity higher than 99.5% at the thermic and spectroscopic analysis.

EXAMPLE 4

Preparation of the salt of S-Ibuprofen with L-lysine

S-Ibuprofen (412.54 g) is put into a planetary mixing-machine and heated up to melting.

Boiling water (about 206 g) is added under stirring.

L-lysine (292.68 g) is then added always under stirring.

The mixture is mixed up to obtain a creamy and homogenous mass.

The mass is then dried in oven.

The salt of S-Ibuprofen with L-lysine (quantitative yield) is obtained and the thermic and spectroscopic analysis show a purity higher than 99.5%.

What we claim is:

1. A process for the preparation of salts of 2-(4-isobutylphenyl)propionic acid with a basic aminoacid, comprising the steps of:

melting said 2-(4-isobutylphenyl)propionic acid;

adding boiling water and an equimolar amount, based on said 2-(4-isobutylphenyl)propionic acid, of a basic aminoacid to the melted 2-(4-isobutylphenyl)propionic acid to form a salt; and, removing the water to isolate said salt.

2. The process according to claim 1, wherein 2-(4-isobutylphenyl)propionic acid is racemic.

3. The process according to claim 1, wherein 2-(4-isobutylphenyl)propionic acid has an S absolute configuration.

4. The process according to claim 1, wherein said basic aminoacid is a member selected from the group consisting of L-arginine and L-lysine.

5. The process according to claim 1, wherein said water is present in an amount of from 0.4 to 1.5 parts by weight with respect to the amount of 2-(4-isobutylphenyl)propionic acid.

6. The process according to claim 1, wherein said water is present in an amount of about 0.5 parts by weight with respect to the amount of 2-(4-isobutylphenyl)propionic acid.

7. The process according to claim 1, wherein 2-(4-isobutylphenyl)propionic acid is racemic and said basic aminoacid is L-arginine.

8. The process according to claim 1, wherein 2-(4-isobutylphenyl)propionic acid is (S)-2-(4-isobutylphenyl)propionic acid and said basic aminoacid is L-arginine.

9. The process according to claim 1, wherein 2-(4-isobutylphenyl)propionic acid is racemic and said basic aminoacid is L-lysine.

10. The process according to claim 1, wherein 2-(4-isobutylphenyl)propionic acid is (S)-2-(4-isobutylphenyl)propionic acid and said basic aminoacid is L-lysine.

* * * * *